United States Patent
Chen et al.

(10) Patent No.: US 11,332,393 B2
(45) Date of Patent: May 17, 2022

(54) AUTO JARTEST ANALYZER

(71) Applicant: ANATEK ENTERPRISE CO., LTD., Koahsiung (TW)

(72) Inventors: Yu-Ming Chen, Koahsiung (TW); Hsiu-Chih Ku, Koahsiung (TW); Jau-Shiu Chen, Koahsiung (TW)

(73) Assignee: ANATEK ENTERPRISE CO., LTD., Koahsiung (TW)

( * ) Notice: Subject to any disclaimer, the term of this patent is extended or adjusted under 35 U.S.C. 154(b) by 113 days.

(21) Appl. No.: 16/820,075

(22) Filed: Mar. 16, 2020

(65) Prior Publication Data

US 2020/0290903 A1 Sep. 17, 2020

(51) Int. Cl.
| | |
|---|---|
| *B01D 21/28* | (2006.01) |
| *B01D 21/30* | (2006.01) |
| *C02F 1/52* | (2006.01) |
| *C02F 1/66* | (2006.01) |
| *G01N 33/18* | (2006.01) |

(Continued)

(52) U.S. Cl.
CPC .............. *C02F 1/66* (2013.01); *B01D 21/286* (2013.01); *B01D 21/305* (2013.01); *B01D 21/32* (2013.01);

(Continued)

(58) Field of Classification Search
CPC .......... C02F 1/66; C02F 1/5209; C02F 1/008; C02F 2209/11; C02F 2209/06; C02F 2209/006; C02F 1/5245; C02F 1/56; C02F 1/52; C02F 1/5236; C02F 1/68; C02F 1/686; G01N 33/1826; G01N 21/82; G01N 1/10; G01N 2001/1031; G01N 33/18; G01N 33/1806; B01L 3/00; B01L 2200/0631; B01J 19/18; B01J 2219/00247; B01J 2219/00479; B01J 2219/00481; B01J 2219/00889; B01J 2219/00905; B01D 21/00; B01D 21/0084; B01D 21/0087; B01D 21/01; B01D 21/245; B01D 21/28;

(Continued)

(56) References Cited

U.S. PATENT DOCUMENTS 4,170,553 A * 10/1979 Lang ...................... B01D 21/01
137/3
5,135,662 A * 8/1992 Ho ........................ G01N 21/534
210/709

(Continued)

*Primary Examiner* — Joseph W Drodge
(74) *Attorney, Agent, or Firm* — Chun-Ming Shih; Lanway IPR Services (57) ABSTRACT

An auto jartest analyzer includes a plurality of water sample reaction equipment, coagulant providing/controlling equipment and a coagulant concentration analysis device. The coagulant providing/controlling equipment provides coagulant of different concentration to the plurality of water sample reaction equipment to allow contaminants in a water sample of the water sample reaction equipment to precipitate. The coagulant concentration analysis device analyzes turbidity measurements for the plurality of water sample reaction equipment and determines if they meet predetermined analysis criteria, so as to figure out an optimal concentration of coagulant currently required to be added to the water sample. This thus achieves automatic analysis of an addition concentration of coagulant to be added to the water sample, which not only improves operational efficiency but also makes the analysis result more accurate.

20 Claims, 7 Drawing Sheets

(51) Int. Cl.
*C02F 1/00* (2006.01)
*B01D 21/32* (2006.01)

(52) U.S. Cl.
CPC ............ *C02F 1/008* (2013.01); *C02F 1/5209* (2013.01); *G01N 33/1826* (2013.01); *C02F 2209/06* (2013.01); *C02F 2209/11* (2013.01)

(58) Field of Classification Search
CPC .... B01D 21/286; B01D 21/30; B01D 21/305; B01D 21/32
See application file for complete search history.

(56) References Cited

U.S. PATENT DOCUMENTS

| | | | |
|---|---|---|---|
| 6,241,896 B1 * | 6/2001 | La Fargue, Jr. | C02F 1/5209 210/143 |
| 10,338,631 B1 * | 7/2019 | Jorden | G01N 21/01 |
| 2005/0127008 A1 * | 6/2005 | Abu-Orf | C02F 1/008 210/723 |
| 2006/0160226 A1 * | 7/2006 | Johnson | C02F 1/5209 436/56 |
| 2008/0288111 A1 * | 11/2008 | Yamaguchi | C02F 1/5209 700/271 |
| 2011/0266227 A1 * | 11/2011 | Yamaguchi | C02F 1/5209 210/709 |
| 2012/0060592 A1 * | 3/2012 | Vercruysse | G01F 11/24 73/64.56 |
| 2015/0259230 A1 * | 9/2015 | Li | C02F 1/688 210/709 |
| 2016/0223452 A1 * | 8/2016 | Milosevic | G03B 15/03 |
| 2017/0297929 A1 * | 10/2017 | Whitaker | C02F 1/5209 |
| 2019/0270655 A1 * | 9/2019 | Jorden | G01N 33/18 |
| 2020/0079661 A1 * | 3/2020 | Criswell | B03D 1/1431 |
| 2020/0308021 A1 * | 10/2020 | Kleinguetl | C02F 1/24 |

\* cited by examiner

AUTO JARTEST ANALYZER

CROSS-REFERENCE TO RELATED APPLICATIONS

This application claims the priority of Republic of China Patent Application Nos. 108108741 filed on Mar. 14, 2019, in the State Intellectual Property Office of the R.O.C., the disclosure of which is incorporated herein by reference.

BACKGROUND OF THE INVENTION

Field of the Invention

The present invention relates to auto jartest analyzer, and more particularly, to an auto jartest analyzer for analyzing concentrations of coagulant to be added.

Descriptions of the Related Art

Coagulation and flocculation are important procedures in the wastewater treatment process. Those procedures are performed by adding coagulant of a predetermined concentration to wastewater that is to be treated, adjusting the wastewater to a desirable pH value, and then adding flocculant to allow flocculation, so as to flocculate and precipitate suspended solids with particle size between 0.1 nm($10^{-7}$ mm)~100 μm($10^{-1}$ mm) that usually disperse and do not easily settle in the wastewater. This is thus to reduce the suspended solids in the wastewater.

The wastewater to be treated flows, which means its water quality may change at any time. However, currently it relies on manual experiment and analysis of what concentration of coagulant to be added to the wastewater. This manually experimental method includes the following steps: getting 5-6 glasses, putting a certain amount of the same water sample in each of the glasses, preparing coagulant of different 5-6 concentrations, adding those different concentrations of coagulant respectively to the glasses by syringes, using a blade mixer to quickly mix the coagulant and water in each of the glasses until thorough mixing is reached, keeping mixing and adding a certain amount of alkali/acid to each of the glasses by syringes, in the meantime using a pH meter to test a pH value of the water sample in each of the glasses and stopping mixing when the water sample in each of the glasses reaches a desirable range of pH values for flocculation to take place, adding a certain amount of flocculant to each of the glasses by syringes, and in each of the glasses slowly mixing the water sample and flocculant until they are thoroughly mixed, and letting suspended solids in the water sample of each of the glasses settle by gravity and precipitate in the bottom of the glass. Then, from "human eye" direct observation or by measuring turbidity of the water sample in each of the glasses, the glass having water sample with the lowest turbidity can be determined and the concentration of coagulant added to this glass is chosen as the optimal concentration of coagulant.

The above manually experimental method is however not good enough as it needs complicated and time-consuming analysis. What may happen is, if there is any delay in analyzing the amount of coagulant to be added, analysis results fail to immediately reflect any change in water quality of the wastewater being tested. Whenever the concentration of suspended solids in the wastewater changes, the amount of coagulant being added fails to immediately respond to that change either. This can cause contamination in water or poor sediment of suspended solids due to insufficient amount of coagulant being added, or cause undesirable raise in cost due to too much coagulant being added.

Moreover, the above manually experimental method uses normal syringes to add coagulant and flocculant, which however brings about measurement errors and human errors, thereby making analysis results inaccurate. A person who operates this method must repeat adding alkali/acid and wait for the water sample in the glasses to reach the desirable range of pH values. This is quite time-ineffective. Further, "human eye" direct observation, rather than using any instrument, is usually taken for quickly determining the water sample with the lowest turbidity. This is definitely not accurate enough.

Therefore, how to solve the above problems encountered in the current manually experimental method, by an automatic design, is an important task in the art.

SUMMARY OF THE INVENTION

In view of the above drawbacks in the conventional technology, a primary object of the invention is to provide an auto jartest analyzer for analyzing a concentration of coagulant to be added to a water sample to allow contaminants in the water sample to precipitate.

According to another purpose of the invention is to provide an auto jartest analyzer for analyzing a concentration of coagulant to be added to improves operational efficiency but also makes the analysis result more accurate.

To achieve the above and other objects, an auto jartest analyzer for analyzing a concentration of coagulant to be added to a water sample to allow contaminants in the water sample to precipitate, the auto jartest analyzer including: a water sample reaction equipment group including a plurality of water sample reaction equipment, each of the water sample reaction equipment including: a reactor having a receiving space for receiving a predetermined amount of the water sample; a coagulant provider for providing coagulant of a predetermined concentration to the water sample in the receiving space so as to make the coagulant and the water sample mix and form a water sample mixture; a pH value measuring device for measuring a pH value of the water sample mixture in the receiving space; an alkali/acid provider for providing acid or alkali to the water sample mixture in the receiving space so as to make the water sample mixture have a predetermined pH value; a flocculant provider for providing flocculant to the receiving space, wherein the flocculant is mixed with the water sample mixture in the receiving space to make contaminants in the water sample mixture precipitate and reduce turbidity of the water sample mixture and a turbidity measuring device for measuring the turbidity of the water sample mixture in the receiving space and sending out a turbidity measurement; coagulant providing/controlling equipment for supplying the coagulant to the coagulant provider of each of the water sample reaction equipment, wherein the coagulant providing/controlling equipment provides the coagulant of different concentrations to the plurality of water sample reaction equipment respectively and a coagulant concentration analysis device for receiving the turbidity measurement from the turbidity measuring device of each of the water sample reaction equipment and for analyzing all the turbidity measurements to find at least one of the turbidity measurements which meets predetermined analysis criteria, wherein the concentration of coagulant provided by the coagulant provider to the water sample reaction equipment corresponding to the found at least one turbidity measurement is used as an addition concentration of the coagulant to be added to the water sample.

Preferably, in the auto jartest analyzer said above, wherein the water sample reaction equipment group includes first water sample reaction equipment, second water sample reaction equipment and third water sample reaction equipment, and the auto jartest analyzer further includes a control device for controlling the first water sample reaction equipment, the second water sample reaction equipment, the third water sample reaction equipment, the coagulant providing/controlling equipment and the coagulant concentration analysis device to perform analysis operations, wherein the control device includes: a setting unit for setting a standard concentration, a standard deviation, a standard turbidity range and a count value; a concentration calculating unit for calculating a high concentration and a low concentration according to the standard concentration and the standard deviation and an execution unit for controlling the first water sample reaction equipment, the second water sample reaction equipment, the third water sample reaction equipment, the coagulant providing/controlling equipment and the coagulant concentration analysis device to perform at least one set of analysis operations including: having the coagulant providing/controlling equipment provide the coagulant of the low concentration to the first water sample reaction equipment, provide the coagulant of the standard concentration to the second water sample reaction equipment, and provide the coagulant of the high concentration to the third water sample reaction equipment; having the first water sample reaction equipment, the second water sample reaction equipment and the third water sample reaction equipment perform water sample reaction operations, such that the first water sample reaction equipment sends out a first turbidity measurement, the second water sample reaction equipment sends out a second turbidity measurement, and the third water sample reaction equipment sends out a third turbidity measurement; and having the coagulant concentration analysis device analyze the first turbidity measurement, the second turbidity measurement and the third turbidity measurement to see if they meet the standard turbidity range, so as to allow the standard concentration, the high concentration and the low concentration to be adjusted according to the analysis result from the coagulant concentration analysis device.

Preferably, in the auto jartest analyzer said above, wherein the control device further includes a parameter adjusting unit, wherein when the coagulant concentration analysis device determines that all the first turbidity measurement, the second turbidity measurement and the third turbidity measurement do not meet the standard turbidity range, the parameter adjusting unit keeps the standard concentration unchanged and updates the count value to calculate a number of times of the analysis result continuously outputted from the coagulant concentration analysis device that all the first turbidity measurement, the second turbidity measurement and third turbidity measurement do not meet the standard turbidity range, and the concentration calculating unit is allowed to update the high concentration and the low concentration according to the standard concentration and the count value, so as to adjust parameters corresponding to the standard concentration, high concentration and low concentration, wherein the low concentration is a difference between the standard concentration and a product of the standard deviation and the count value, and the high concentration is a sum of the standard concentration and a product of the standard deviation and the count value.

Preferably, in the auto jartest analyzer said above, wherein the at least one set of analysis operations includes a plurality of sets of analysis operations, and wherein when the number of times of the analysis result continuously outputted from the coagulant concentration analysis device that all the first turbidity measurement, the second turbidity measurement and the third turbidity measurement do not meet the standard turbidity range, reaches a predetermined number of times during each of the plurality of sets of analysis operations, the execution unit is further allowed to stop the analysis operations.

Preferably, in the auto jartest analyzer said above, wherein the control device further includes a parameter adjusting unit, wherein when the coagulant concentration analysis device determines that at least two of the first turbidity measurement, the second turbidity measurement and the third turbidity measurement meet the standard turbidity range, the parameter adjusting unit selects the concentration of coagulant, which corresponds to the lowest one of the at least two of the first turbidity measurement, the second turbidity measurement and the third turbidity measurement, to be the standard concentration, and the concentration calculating unit is allowed to update the low concentration and the high concentration according to the standard concentration, so as to adjust parameters corresponding to the standard concentration, high concentration and low concentration, wherein the high concentration is a sum of the standard concentration and the standard deviation, and the low concentration is a difference between the standard concentration and the standard deviation.

Preferably, in the auto jartest analyzer said above, wherein when the coagulant concentration analysis device determines that all the first turbidity measurement, the second turbidity measurement and the third turbidity measurement meet the standard turbidity range and are identical, the parameter adjusting unit keeps the standard concentration, the high concentration and the low concentration unchanged.

Preferably, in the auto jartest analyzer said above, wherein the control device further includes a parameter adjusting unit, wherein when the coagulant concentration analysis device determines that only one of the first turbidity measurement, the second turbidity measurement and the third turbidity measurement meets the standard turbidity range, the parameter adjusting unit selects the concentration of coagulant, which corresponds to the determined one of the first turbidity measurement, the second turbidity measurement and the third turbidity measurement, to be the standard concentration, and the concentration calculating unit is allowed to update the low concentration and the high concentration according to the standard concentration, wherein the high concentration is a sum of the standard concentration and the standard deviation, and the low concentration is a difference between the standard concentration and the standard deviation, so as to adjust parameters corresponding to the standard concentration, high concentration and low concentration.

Preferably, in the auto jartest analyzer said above, wherein the control device further includes a parameter adjusting unit, wherein when the coagulant concentration analysis device determines that at least two of the first turbidity measurement, the second turbidity measurement and the third turbidity measurement meet the standard turbidity range, the parameter adjusting unit selects the lowest one of the concentrations of coagulant corresponding to the at least two of the first turbidity measurement, the second turbidity measurement and the third turbidity measurement, to be the standard concentration, and the concentration calculating unit is allowed to update the low concentration and the high concentration according to the standard concentration, so as to adjust parameters corresponding to the standard concentration, high concentration and low concentration, wherein the high concentration is a sum of the standard concentration and the standard deviation, and the low concentration is a difference between the standard concentration and the standard deviation.

Preferably, in the auto jartest analyzer said above, wherein the control device further includes a parameter adjusting unit, wherein when the coagulant concentration analysis device determines that at least two of the first turbidity measurement, the second turbidity measurement and the third turbidity measurement meet the standard turbidity range, the parameter adjusting unit selects the highest one of the concentrations of coagulant corresponding to the at least two of the first turbidity measurement, the second turbidity measurement and the third turbidity measurement, to be the standard concentration, and the concentration calculating unit is allowed to update the low concentration and the high concentration according to the standard concentration, so as to adjust parameters corresponding to the standard concentration, high concentration and low concentration, wherein the high concentration is a sum of the standard concentration and the standard deviation, and the low concentration is a difference between the standard concentration and the standard deviation.

Preferably, in the auto jartest analyzer said above, further including a cleaning device, wherein the at least one set of analysis operations includes a plurality of sets of analysis operations, and the control device is further allowed to control the cleaning device to clean the first water sample reaction equipment, the second water sample reaction equipment and the third water sample reaction equipment before or after the execution unit performs each of the plurality of sets of analysis operations.

Preferably, in the auto jartest analyzer said above, further including a cleaning device, wherein the at least one set of analysis operations includes a plurality of sets of analysis operations, and the control device is further allowed to control the cleaning device to clean the first water sample reaction equipment, the second water sample reaction equipment and the third water sample reaction equipment after the execution unit performs a predetermined one of the plurality of sets of analysis operations.

Preferably, in the auto jartest analyzer said above, wherein the cleaning device includes a pickling agent provider, a primary cleaning fluid provider and a secondary cleaning fluid provider, wherein the pickling agent provider provides a pickling agent to the receiving space, the primary cleaning fluid provider provides a primary cleaning fluid at a primary location to the receiving space, and the secondary cleaning fluid provider provides a secondary cleaning fluid at a secondary location to the receiving space, wherein the pickling agent, the primary cleaning fluid and the secondary cleaning fluid are for cleaning a precipitate in the receiving space and the secondary cleaning fluid is further for cleaning the precipitate on the pH value measuring device.

Preferably, in the auto jartest analyzer said above, wherein each of the water sample reaction equipment further includes a primary stirring unit and a secondary stirring unit, wherein the primary stirring unit is for providing a primary stirring force for thoroughly mixing the water sample, the coagulant, and the acid or the alkali in the receiving space, and the secondary stirring unit is for providing a secondary stirring force for mixing the water sample and the flocculant in the receiving space, wherein the secondary stirring force is weaker than the primary stirring force and is favorable for better precipitation in the water sample mixture.

Preferably, in the auto jartest analyzer said above, when the pickling agent and the primary cleaning fluid are cleaning the precipitate in the receiving space, the primary stirring unit can exert a primary stirring force on the receiving space respectively to make the pickling agent and the primary cleaning fluid being stirred in the receiving space to thereby optimize the cleaning effect on the precipitate.

Preferably, in the auto jartest analyzer said above, the primary stirring unit and the secondary stirring unit use, for example, airflow, blades or magnets to provide the primary stirring force and the secondary stirring force respectively.

The invention is also provide an automatic analysis method for the automatic analysis said above, including the steps of: having the coagulant providing/controlling equipment provide the coagulant of different concentrations to the receiving space of each of the plurality of water sample reaction equipment respectively so as to form a water sample mixture of different composition in the receiving space of each of the water sample reaction equipment; having the alkali/acid provider of each of the water sample reaction equipment provide acid or alkali to the water sample mixture in the receiving space until the water sample mixture reaches a predetermined pH value; having the flocculant provider of each of the water sample reaction equipment provide the flocculant to the water sample mixture in the receiving space, so as to allow contaminants of the water sample mixture to precipitate in the receiving space and reduce turbidity; having the turbidity measuring device of each of the water sample reaction equipment measure turbidity of the water sample mixture in the receiving space; having the coagulant concentration analysis device analyze which turbidity measurement meets predetermined analysis criteria and determine its corresponding water sample reaction equipment, wherein the concentration of coagulant of the determined water sample reaction equipment is used as an addition concentration of the coagulant to be added to the water sample.

Compared to prior arts, the present invention is to provide an auto jartest analyzer, which automatically analyzes a required concentration of coagulant to be added to a water sample to allow contaminants in the water sample to precipitate in a way that, the analysis result of the concentration of coagulant to be added immediately responds to current water quality of the water sample, so as to accurately calculate an exact amount of coagulant required for the water sample, thereby avoiding any water contamination caused by adding an incorrect amount of coagulant.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Embodiments of the present invention will now be described in detail with reference to the accompanying drawings. The invention may, however, be embodied in many different forms and should not be construed as being limited to the embodiments set forth herein. Rather, these embodiments are provided so that this disclosure will be thorough and complete, and will fully convey the scope of the invention to those skilled in the art. In the drawings, the shapes and dimensions of elements may be exaggerated for clarity, and the same reference numerals will be used throughout to designate the same or like components.

Figure 1:
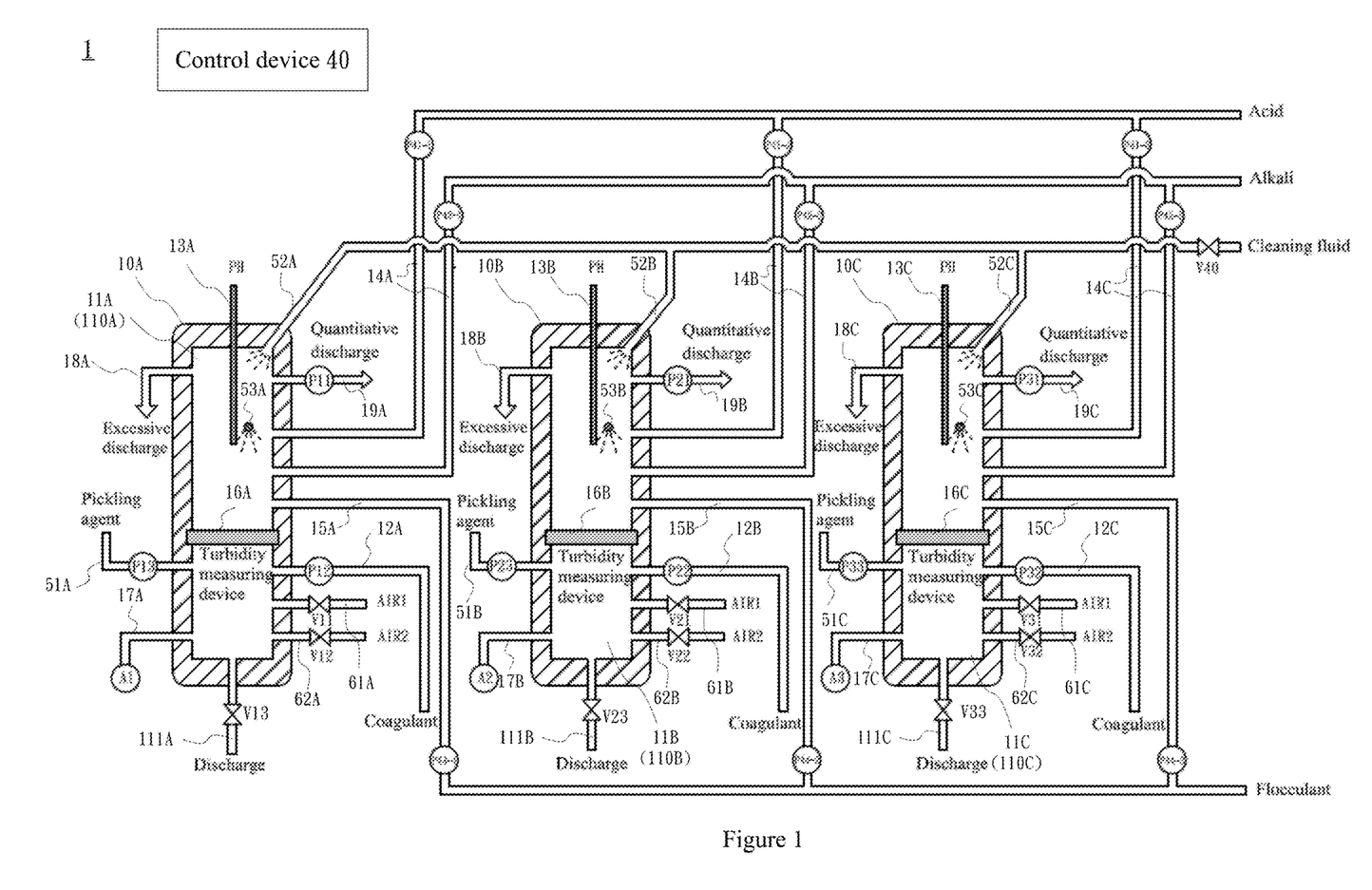
FIG. 1 is an architectural diagram of an auto jartest analyzer according to the present invention.
Figure 3A:
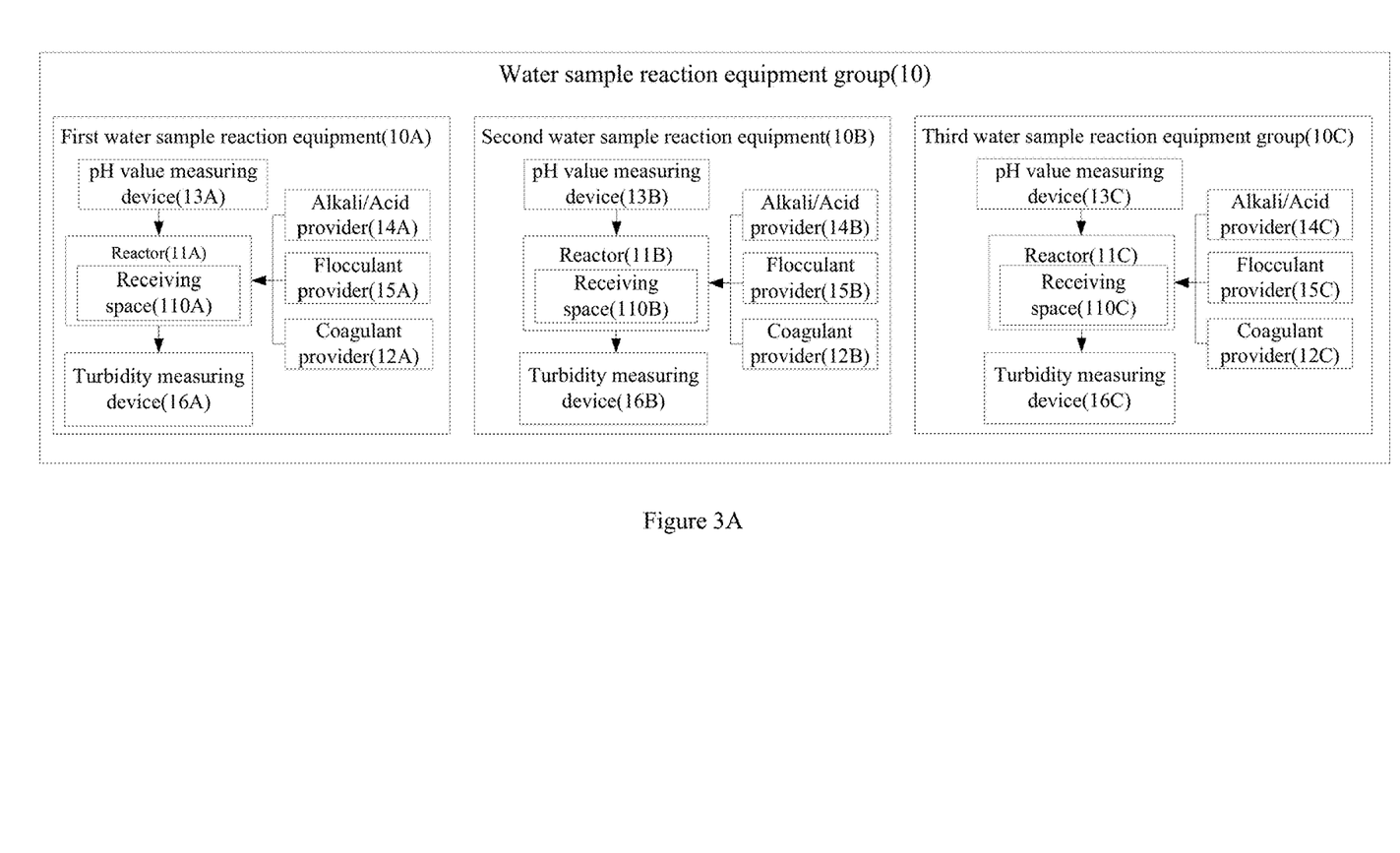
FIGS. 3A and 3B are architectural diagrams of the auto jartest analyzer according to the present invention.
Figure 3B:
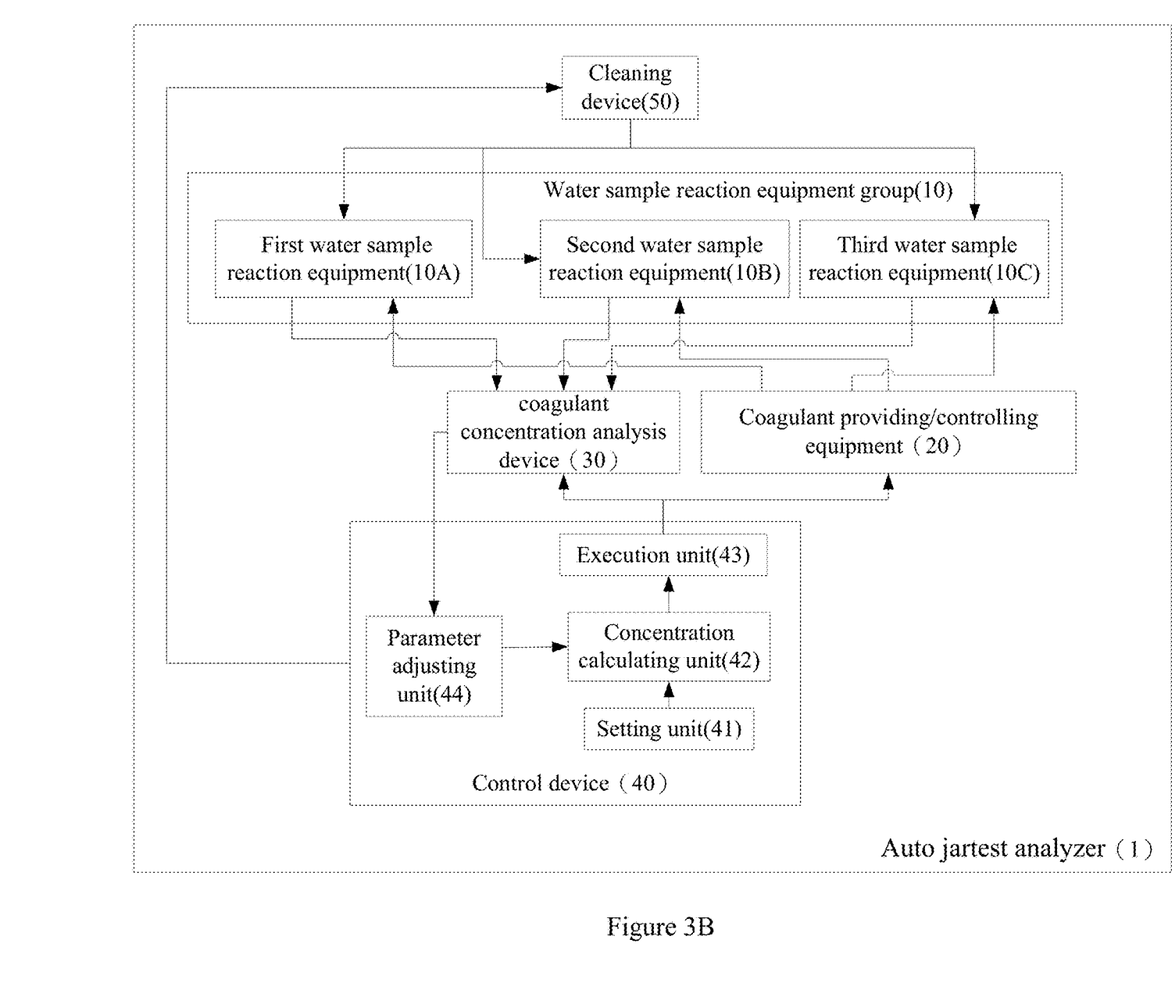

Referring to FIGS. 1 and 3B, the present invention provides an auto jartest analyzer 1 for analyzing a concentration of coagulant to be added to a water sample to allow contaminants in the water sample to precipitate. As shown in the figure, the auto jartest analyzer 1 includes: a water sample reaction equipment group 10, coagulant providing/controlling equipment 20 and a coagulant concentration analysis device 30. The water sample is for example wastewater discharged by a factory.

Referring to FIGS. 1 and 3A, the water sample reaction equipment group 10 includes a plurality of water sample reaction equipment, such as first water sample reaction equipment 10A, second water sample reaction equipment 10B and third water sample reaction equipment 10C. It should be noted that, the number of water sample reaction equipment included in the water sample reaction equipment group 10 is not limited to three, but can be flexibly adjusted according to practical requirements. Each of the water sample reaction equipment 10A/10B/10C has basically same architecture, and respectively includes: a reactor 11A/11B/11C, a coagulant provider 12A/12B/12C, a pH value measuring device 13A/13B/13C, an alkali/acid provider 14A/14B/14C, a flocculant provider 15A/15B/15C and a turbidity measuring device 16A/16B/16C.

The reactor 11A/11B/11C includes a receiving space 110A/110B/110C for receiving a predetermined amount of the water sample. The water sample reaction equipment 10A/10B/10C respectively further includes an inlet controller 17A/17B/17C, an excess outlet 18A/18B/18C and a quantitative outlet 19A/19B/19C. The inlet controller 17A/17B/17C is connected to an inlet A1/A2/A3 and the bottom of the receiving space 110A/110B/110C, and is used to deliver the water sample inputted from the inlet A1/A2/A3 to the receiving space 110A/110B/110C of the reactor 11A/11B/11C respectively. The inlet controller 17A/17B/17C also includes a valve (not shown). The valve can be activated to allow the water sample to flow upwards into the receiving space 110A/110B/110C.

Figure 2:
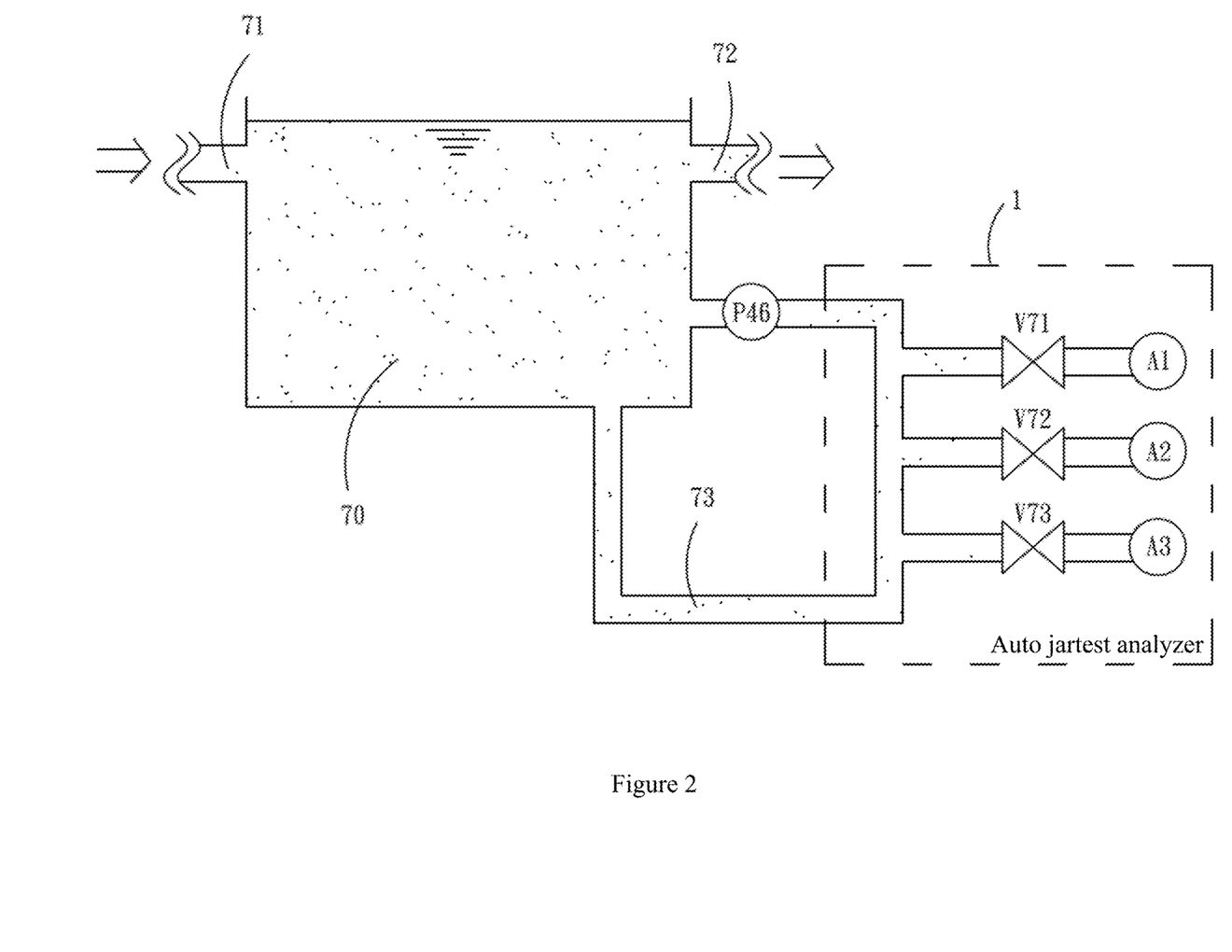
FIG. 2 is a structural diagram of a treatment tank according to the present invention.

FIG. 2 is an architectural diagram of a treatment tank 70 according to a preferred embodiment of the present invention, wherein the treatment tank 70 can be mounted at a front end of the auto jartest analyzer 1. The treatment tank 70 includes: an input pipe 71 and an output pipe 72, wherein the input pipe 71 is used to input wastewater from a factory to the treatment tank 70, and the output pipe 72 is used to output wastewater from the treatment tank 70. The treatment tank 70 further includes a circulation pipe 73, wherein a pump P46 is mounted on the circulation pipe 73 and can be activated to allow the water sample in the circulation pipe 73 and the water sample in the treatment tank 70 to circulate. The inlet A1/A2/A3 is respectively connected to the circulation pipe 73 by a valve V71/V72/V73. By activating the valve V71/V72/V73, the water sample in the circulation pipe 73 can be driven to flow into the inlet A1/A2/A3 simultaneously to be delivered to the water sample reaction equipment 10A/10B/10C shown in FIG. 1. This assures the water sample of consistent water quality to be delivered to the water sample reaction equipment 10A/10B/10C and thus improves accuracy of subsequent analysis results.

The excess outlet 18A/18B/18C is connected to an upper part of the receiving space 110A/110B/110C, and is used to discharge any excess water sample from the receiving space 110A/110B/110C, that is to discharge any water sample from the receiving space 110A/110B/110C at a level higher than a water level in the receiving space 110A/110B/110C corresponding to the excess outlet 18A/18B/18C. The quantitative outlet 19A/19B/19C is also connected to the receiving space 110A/110B/110C. The quantitative outlet 19A/19B/19C is located corresponding to a water level in the receiving space 110A/110B/110C lower than that corresponding to the excess outlet 18A/18B/18C, and is used to discharge part of the water sample from the receiving space 110A/110B/110C, that is to discharge any water sample from the receiving space 110A/110B/110C at a level higher than the water level corresponding to the quantitative outlet 19A/19B/19C, so as to make the receiving space 110A/110B/110C only receive the same predetermined amount of water sample. In a preferred embodiment, the quantitative outlet 19A/19B/19C is respectively provided with a pump P11/P21/P31 for water discharge.

The receiving space 110A/110B/110C can further include a discharge unit 111A/111B/111C in the bottom thereof respectively, for discharging the water sample from the bottom of the receiving space 110A/110B/110C. In a preferred embodiment, the discharge unit 111A/111B/111C further includes a valve V13/V23/V33 respectively for switching an on/off status of the discharge unit 111A/111B/111C.

The coagulant provider 12A/12B/12C is used to respectively provide coagulant of different concentrations to the water sample in the receiving space 110A/110B/110C, so as to make the coagulant and the water sample in the receiving space 110A/110B/110C mix and form a water sample mixture (to be described later). Coagulant here is for example, but not limited to, iron salt or aluminum salt.

The pH value measuring device 13A/13B/13C is used to measure a pH value of the water sample mixture in the receiving space 110A/110B/110C respectively.

The alkali/acid provider 14A/14B/14C is used to provide alkali or acid to the water sample mixture (that is the mixture of coagulant and water sample) in the receiving space 110A/110B/110C respectively, so as to make the pH value of the water sample mixture reach a predetermined pH value. Acid here is for example, but not limited to, sulfuric acid, and alkali here is for example, but not limited to, sodium hydroxide. Moreover, as shown in FIG. 1, a pump P41-1/P41-2/P41-3 is further mounted on an acid pipe of the alkali/acid provider 14A/14B/14C respectively, and a pump P42-1/P42-2/P42-3 is further mounted on an alkali pipe of the alkali/acid provider 14A/14B/14C respectively.

The flocculant provider 15A/15B/15C is used to respectively provide flocculant to the receiving space 110A/110B/110C, so as to make the flocculant mix and react with the water sample mixture in the receiving space 110A/110B/110C to precipitate contaminants in the water sample mixture and thus reduce turbidity of the water sample mixture. Flocculant here is for example, but not limited to, oxidant, loading agent or polyelectrolyte. Moreover, the flocculant provider 15A/15B/15C of the water sample reaction equipment 10A/10B/10C further includes a pump P44-1/P44-2/P44-3 respectively that can all be connected to the same flocculant inlet.

The turbidity measuring device 16A/16B/16C is used to respectively measure turbidity of the water sample mixture in the receiving space 110A/110B/110C and send out a corresponding turbidity measurement.

The water sample reaction equipment 10A/10B/10C respectively further includes a primary stirring unit 61A/61B/61C and a secondary stirring unit 62A/62B/62C. The primary stirring unit 61A/61B/61C is used to provide a primary stirring force for quickly mixing the water sample, coagulant, and acid or alkali in the receiving space 110A/110B/110C thoroughly. The secondary stirring unit 62A/62B/62C is used to provide a secondary stirring force for quickly mixing the water sample and flocculant in the receiving space 110A/110B/110C thoroughly. The primary stirring unit 61A/61B/61C and the secondary stirring unit 62A/62B/62C use, for example, airflow, blades or magnets to provide the primary stirring force and secondary stirring force respectively, wherein the secondary stirring force is weaker than the primary stirring force and is favorable for better precipitation in the water sample mixture. Preferably, in a preferred embodiment, the primary stirring unit 61A/61B/61C and the secondary stirring unit 62A/62B/62C use airflow to produce primary and secondary stirring forces. Moreover, there is a valve V11/V21/V31 mounted on the primary stirring unit 61A/61B/61C respectively, and there is a valve V12/V22/V32 mounted on the secondary stirring unit 62A/62B/62C respectively.

The coagulant providing/controlling equipment 20 is used to supply coagulant of different concentrations to the coagulant provider 12A/12B/12C of the water sample reaction equipment 10A/10B/10C respectively, to be described in detail later.

The coagulant concentration analysis device 30 is used to receive the corresponding turbidity measurement from the turbidity measuring device 16A/16B/16C of the water sample reaction equipment 10A/10B/10C respectively, and analyze it to find a turbidity measurement that meets predetermined analysis criteria. Then, the coagulant provided by the coagulant provider 12A, 12B or 12C of the water sample reaction equipment 10A, 10B or 10C, which has a concentration corresponding to the found turbidity measurement, is used as an added concentration of coagulant to be added to the water sample.

Moreover, the auto jartest analyzer 1 of the present invention further includes a control device 40 for controlling the first water sample reaction equipment 10A, the second water sample reaction equipment 10B, the third water sample reaction equipment 10C, the coagulant providing/controlling equipment 20 and the coagulant concentration analysis device 30 to perform analysis operations including the following steps to be described with reference to FIGS. 3B, 4A, 4B and 4C.

As shown in FIG. 3B, the control device 40 includes a setting unit 41, a concentration calculating unit 42, an execution unit 43 and a parameter adjusting unit 44. The setting unit 41 is used to set, but not limited to, a standard concentration, a standard deviation, a standard turbidity range and a predetermined count value. It can also set other parameters according to practical requirements, for example, the above analysis criteria used for the analysis operation performed by the coagulant concentration analysis device 30. The concentration calculating unit 42 is used to calculate a high concentration and a low concentration according to the standard concentration and the standard deviation set by the setting unit 41.

The execution unit 43 is used to control the first water sample reaction equipment 10A, the second water sample reaction equipment 10B, the third water sample reaction equipment 10C, the coagulant providing/controlling equipment 20 and the coagulant concentration analysis device 30 to perform at least one set of analysis operations. The parameter adjusting unit 44 is used to adjust the standard concentration of coagulant according to analysis results from the coagulant concentration analysis device 30 when the execution unit 43 has finished a set of analysis operations. This allows the concentration calculating unit 42 to adjust the high concentration and the low concentration according to the adjusted standard concentration.

In a preferred embodiment, the analysis operations performed by the execution unit 43 include the following steps. First, the coagulant providing/controlling equipment 20 is allowed to provide coagulant of the low concentration to the first water sample reaction equipment 10A, provide coagulant of the standard concentration to the second water sample reaction equipment 10B, and provide coagulant of the high concentration to the third water sample reaction equipment 10C. Then, the first water sample reaction equipment 10A, the second water sample reaction equipment 10B, the third water sample reaction equipment 10C is allowed to respectively execute a water sample reaction operation, wherein the first water sample reaction equipment 10A sends out a first turbidity measurement, the second water sample reaction equipment 10B sends out a second turbidity measurement, and the third water sample reaction equipment 10C sends out a third turbidity measurement. Then, the coagulant concentration analysis device 30 is allowed to analyze the first turbidity measurement, the second turbidity measurement and the third turbidity measurement respectively to see if they meet the standard turbidity range set by the setting unit 41, and the standard concentration, high concentration and low concentration are adjusted according to the analysis results.

Figure 4A:
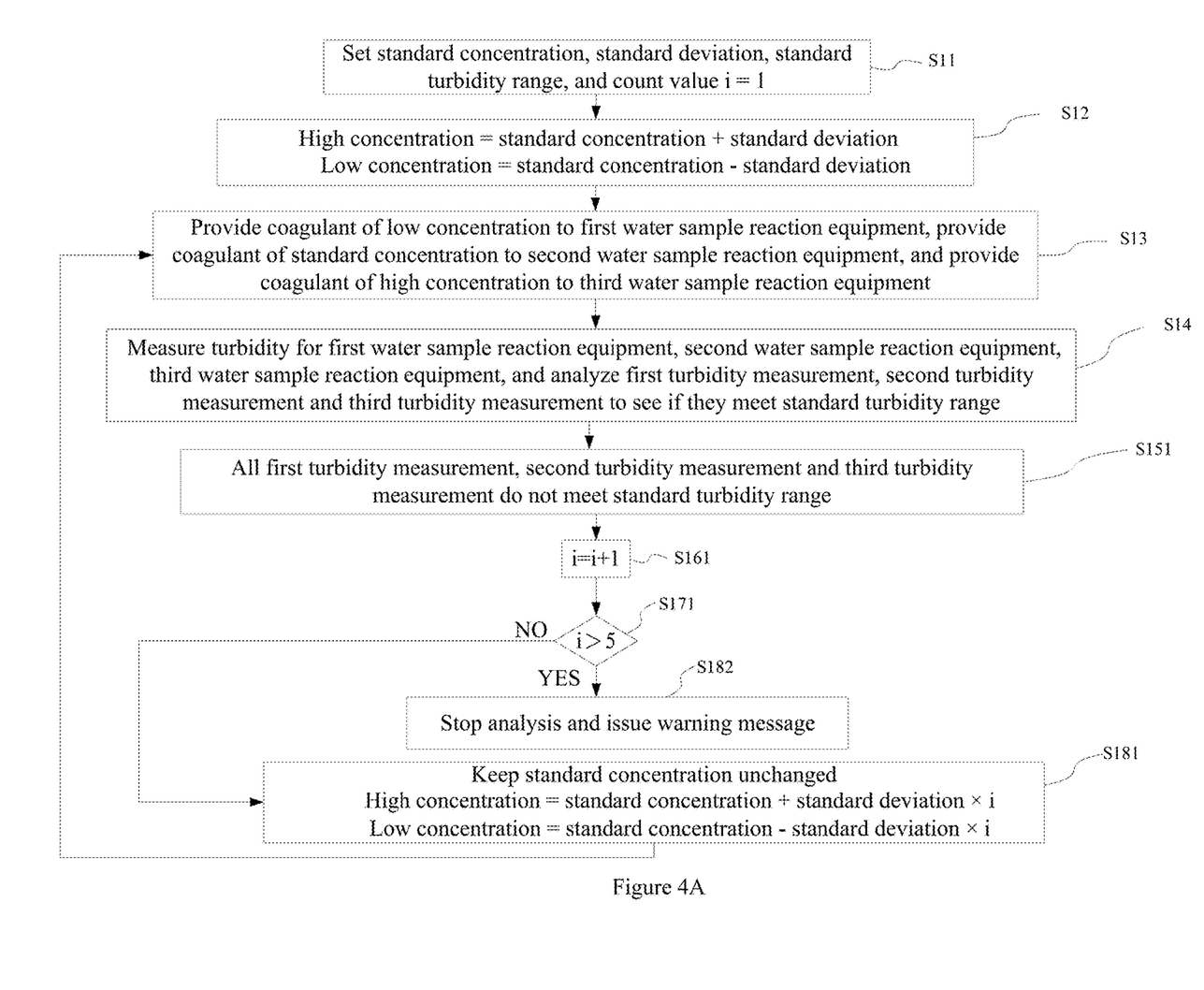
FIGS. 4A to 4C are schematic flowcharts showing different steps of determining standard concentrations by the auto jartest analyzer according to the present invention.
Figure 4B:
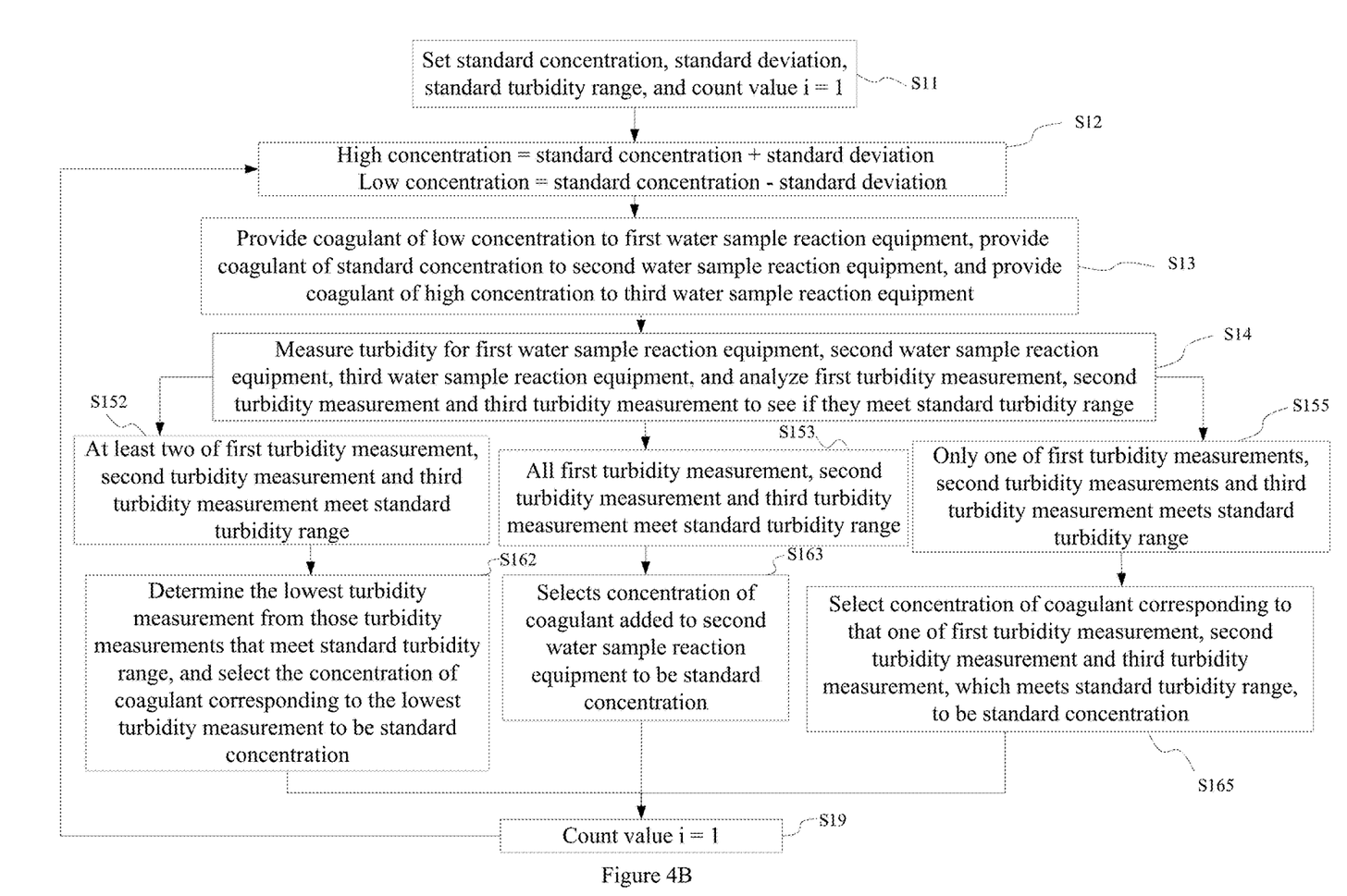

Refer to FIGS. 4A and 4B, which shows a flowchart of steps for adjusting a standard concentration, a high concentration and a low concentration according to a preferred embodiment of the present invention.

First, step S11 is executed to allow the setting unit 41 to set a standard concentration, a standard deviation, a standard turbidity range and a count value, wherein the count value i=1. Then, step S12 is executed.

In step S12, the concentration calculating unit 42 calculates a high concentration and a low concentration according to the standard concentration set by the setting unit 41, wherein the high concentration is the sum of the standard concentration and the standard deviation (that is, high concentration=standard concentration+standard deviation), and the low concentration is the difference between the standard concentration and the standard deviation (that is, low concentration=standard concentration−standard deviation). Then, step S13 is executed.

In step S13, the coagulant providing/controlling equipment 20 provides coagulant of the low concentration to the first water sample reaction equipment 10A, provides coagulant of the standard concentration to the second water sample reaction equipment 10B, and provides coagulant of the high concentration to the third water sample reaction equipment 10C. Then, step S14 is executed. In a preferred embodiment, before each set of analysis operations starts, the coagulant providing/controlling equipment 20, according to the concentration of coagulant to be added, automatically figures out working time intervals of a corresponding pump for adding the coagulant so as to perform addition of different concentrations of coagulant.

In step S14, the turbidity measuring device 16A/16B/16C respectively measures turbidity for the first water sample reaction equipment 10A, the second water sample reaction equipment 10B, the third water sample reaction equipment 10C and sends out the first turbidity measurement, the second turbidity measurement and the third turbidity measurement. Then, the first turbidity measurement, the second turbidity measurement and the third turbidity measurement are analyzed respectively to see if they meet the standard turbidity range set by the setting unit 41. According to the analysis result, one of step S151, step S152, step S153 and step S155 is then selected and executed.

In step S151, the coagulant concentration analysis device 30 analyzes the turbidity measurements and finds that all the first turbidity measurement, the second turbidity measurement and the third turbidity measurement do not meet the standard turbidity range. Then, step S161 is executed.

In step S161, the count value i becomes i+1 (i=i+1). Then, step S171 is executed.

In step S171, it determines if the count value i is larger than 5. If yes (i>5), it means the coagulant concentration analysis device 30 has continuously sent out for five times the analysis result that all the first turbidity measurement, the second turbidity measurement and the third turbidity measurement do not meet the standard turbidity range, and step S182 is executed to stop the analysis operations and issue an abnormality warning. It should be noted that, the upper limit of the count value i is not necessary to be five but can be flexibly adjusted according to practical requirements. If the analysis result shows that the count value i is not larger than 5, step S181 is executed.

In step S181, the parameter adjusting unit 44 remains the current standard concentration, while the concentration calculating unit 42 adjusts the high concentration and the low concentration in a way that, the low concentration becomes the difference between the standard concentration and a product of the standard deviation and the count value (that is, low concentration=standard concentration−standard deviation×i), and the high concentration becomes the sum of the standard concentration and a product of the standard deviation and the count value (that is, high concentration=standard concentration+standard deviation× i). In other words, with the standard concentration being unchanged, the adjusted low concentration is calculated by the standard concentration minus two times of the standard deviation, and the adjusted high concentration is calculated by the standard concentration plus two times of the standard deviation. Then, it returns to and executes step S13, in order to perform a next set of analysis operations.

It should be noted that, the above step S161 is used to calculate how many times of the analysis result being continuously outputted from the coagulant concentration analysis device 30 that all the first turbidity measurement, the second turbidity measurement and the third turbidity measurement do not meet the standard turbidity range. And, step S171 is used to determine whether the number of times of the analysis result being continuously outputted from the coagulant concentration analysis device 30 reaches a predetermined number in order to decide if the analysis operations encounter any abnormal situation. For example, when step S181 completes and it returns to step S13 to perform the next set of analysis operations, if an analysis result from the next set of analysis operations is still the same as that in step S151, that is, consecutive two times of analysis results both show all the first turbidity measurement, the second turbidity measurement and the third turbidity measurement do not meet the standard turbidity range, then the standard concentration is still kept the same, while the low concentration is adjusted and calculated by the standard concentration minus three times of the standard deviation, and the high concentration is adjusted and calculated by the standard concentration plus three times of the standard deviation; and so on. It goes in this way continuously until when the fifth time of analysis result still shows all the first turbidity measurement, the second turbidity measurement and the third turbidity measurement do not meet the standard turbidity range, then the analysis result stays the same as the previous result, and analysis is stopped while a warning message is issued (that is, step S182).

In step S152, the coagulant concentration analysis device 30 analyzes the turbidity measurements and finds that at least two of the first turbidity measurement, the second turbidity measurement and the third turbidity measurement meet the standard turbidity range. Then, step S162 is executed.

In step S162, the parameter adjusting unit 44 determines the lowest turbidity measurement from those turbidity measurements that meet the standard turbidity range and selects the concentration of coagulant corresponding to the lowest turbidity measurement to be the standard concentration. Then, step S19 is executed. This allows continuous automatic monitoring and changing analysis concentrations for the water sample reaction equipment 10A/10B/10C to obtain the lowest turbidity measurement, such that the required amount of coagulant being added can be varied immediately in response to any change in the condition of suspended solids in the water sample being treated.

In step S153, the coagulant concentration analysis device 30 analyzes the turbidity measurements, and finds that all the first turbidity measurement, the second turbidity measurement and the third turbidity measurement meet the standard turbidity range and are identical. Then, step S163 is executed.

In step S163, the parameter adjusting unit 44 remains the current standard concentration, that is, selects the concentration of coagulant added to the second water sample reaction equipment 10B to be the standard concentration, and also keeps the high and low concentrations unchanged. Then, step S19 is executed. This allows continuously stable and identical analysis results to be obtained.

In step S155, the coagulant concentration analysis device 30 analyzes the turbidity measurements and finds that only one of the first turbidity measurement, the second turbidity measurement and the third turbidity measurement meets the standard turbidity range. Then, step S165 is executed.

In step S165, the parameter adjusting unit 44 selects the concentration of coagulant corresponding to that one of the first turbidity measurement, the second turbidity measurement and the third turbidity measurement, which meets the standard turbidity range, to be the standard concentration. Then, step S19 is executed.

In step S19, the count value is set 1 (i=1), which is to stop calculating the number of times of the analysis result being continuously outputted from the coagulant concentration analysis device 30 that all the first turbidity measurement, the second turbidity measurement and the third turbidity measurement do not meet the standard turbidity range. Then, it returns to and executes step S12.

Figure 4C:
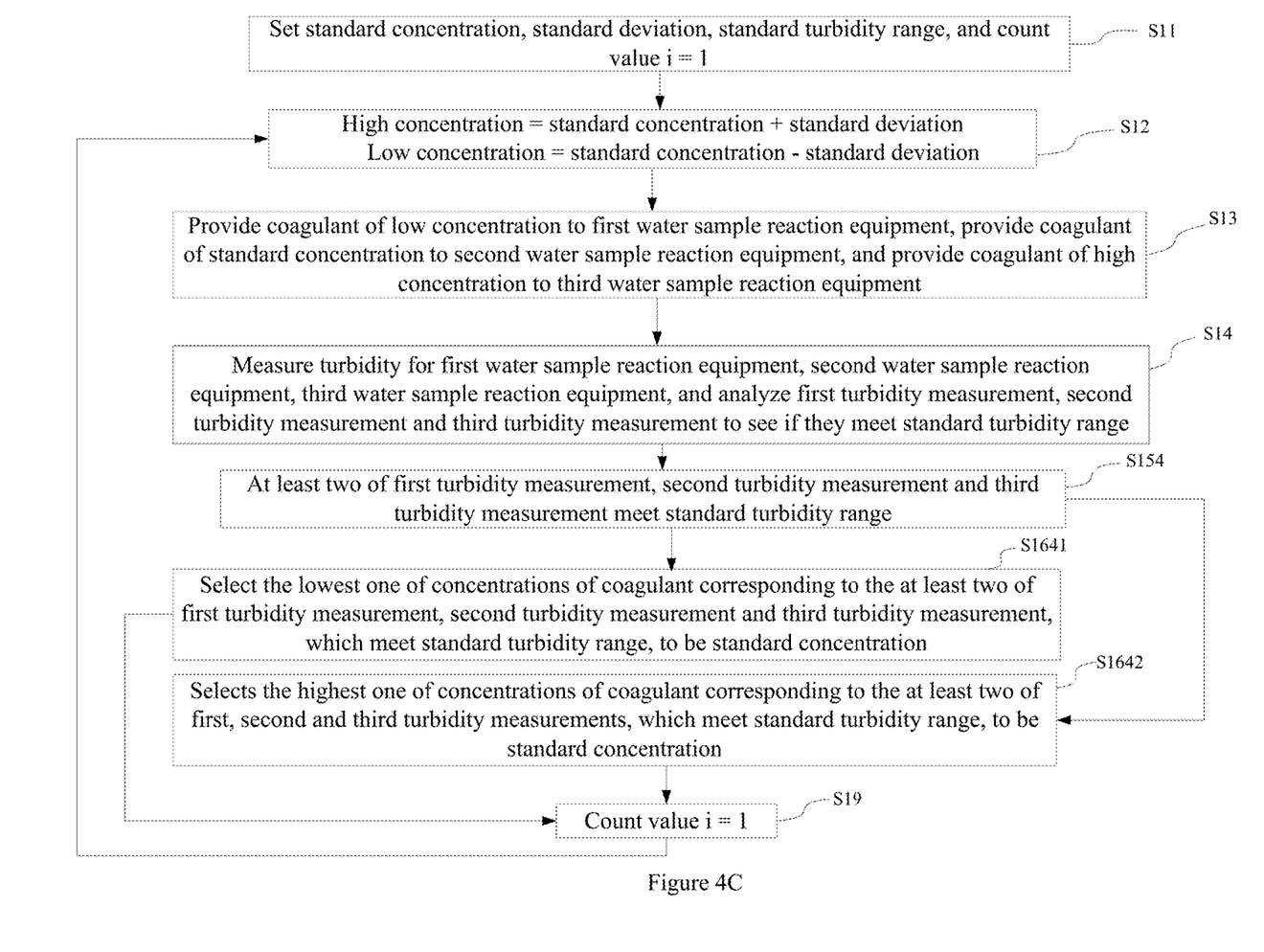

Refer to FIG. 4C, which shows a flowchart of steps for adjusting a standard concentration, a high concentration and a low concentration according to another preferred embodiment of the present invention. The flowchart show in FIG. 4C, step S154 in FIG. 4C replaces steps S152 and 153 in FIG. 4B, in order to customize the analysis of concentration of coagulant to be added.

Particularly, in step S154, when the coagulant concentration analysis device 30 analyzes the turbidity measurements and finds that at least two of the first turbidity measurement, the second turbidity measurement and the third turbidity measurement meet the standard turbidity range, the next operation of adjusting the standard concentration can be executed in a customized way. Customized settings include: (1) selecting and using an analysis concentration of adding the least amount of coagulant (the lowest concentration) in priority, and (2) selecting and using an analysis concentration of adding the most amount of coagulant (the highest concentration) in priority, wherein setting (1) can reduce material (that is, coagulant) cost, while setting (2) meets more strict test criteria and can improve wastewater treatment effects. Setting (2) is usually taken when there is a significant change in water quality of source water (wastewater), so as to make sure wastewater turbidity does not exceed a predetermined limit nor trigger a warning. In a preferred embodiment, when setting (1) is taken, step S1641 is executed; whereas when setting (2) is taken, step S1642 is executed.

In step S1641, the parameter adjusting unit 44 selects the lowest one of the concentrations of coagulant corresponding to the at least two of the first turbidity measurement, the second turbidity measurement and the third turbidity measurement, which meet the standard turbidity range, to be the standard concentration. Then, step S19 is executed.

In step S1642, the parameter adjusting unit 44 selects the highest one of the concentrations of coagulant corresponding to the at least two of the first turbidity measurement, the second turbidity measurement and the third turbidity measurement, which meet the standard turbidity range, to be the standard concentration. Then, step S19 is executed.

As shown in FIG. 3B, the auto jartest analyzer 1 can include a cleaning device 50. The control device 40 can further control the cleaning device 50 to clean the first water sample reaction equipment 10A, the second water sample reaction equipment 10B, the third water sample reaction equipment 10C before or after the execution unit 43 performs each set of analysis operations. In particular, before and after each set of analysis operations is executed, the control device 40 allows the cleaning device 50 to automatically start cleaning operations for glasses and detection electrodes and discharge residual liquid from the reactor 11A/11B/11C.

The control device 40 can further control the cleaning device 50 to clean the first water sample reaction equipment 10A, the second water sample reaction equipment 10B, the third water sample reaction equipment 10C after the execution unit 43 performs a predetermined set of analysis operations. In particular, according to a setting of the number of analysis being completed, the control device 40 allows the cleaning device 50 to automatically start an acid or alkali cleaning process that includes leaching turbidity electrodes, pH electrodes and glasses and then cleaning them with a cleaning fluid.

As shown in FIG. 1, the cleaning device 50 can include a pickling agent provider 51A/51B/51C, a primary cleaning fluid provider 52A/52B/52C and a secondary cleaning fluid provider 53A/53B/53C. The pickling agent provider 51A/51B/51C is used to supply a pickling agent to the receiving space 110A/110B/110C respectively, and the primary cleaning fluid provider 52A/52B/52C is used to supply a primary cleaning fluid at a primary location to the receiving space 110A/110B/110C respectively. A valve V40 (for example, pneumatic valve) can be mounted at a front end of the primary cleaning fluid provider 52A/52B/52C, and allows the primary cleaning fluid to enter the primary cleaning fluid provider 52A/52B/52. The secondary cleaning fluid provider 53A/53B/53C is used to supply a secondary cleaning fluid at a secondary location to the receiving space 110A/110B/110C respectively. The pickling agent, primary cleaning fluid and secondary cleaning fluid being supplied can clean the precipitate in the receiving space 110A/110B/110C. The secondary cleaning fluid provider 53A/53B/53C is located near the pH value measuring device 13A/13B/13C, and the secondary cleaning fluid can also clean the precipitate on the pH value measuring device 13A/13B/13C respectively. When the pickling agent and the primary cleaning fluid act on the precipitate in the receiving space 110A/110B/110C, the primary stirring unit 61A/61B/61C can exert a primary stirring force on the receiving space 110A/110B/110C respectively to make the pickling agent and the primary cleaning fluid being stirred in the receiving space 110A/110B/110C to thereby optimize the cleaning effect on the precipitate.

An automatic analysis method of the auto jartest analyzer 1 according to the present invention includes the steps of: having the coagulant providing/controlling equipment 20 provide coagulant of different concentrations to the receiving space 110A/110B/110C of the water sample reaction equipment 10A/10B/10C respectively so as to form a water sample mixture of different composition in the receiving space 110A/110B/110C of the water sample reaction equipment 10A/10B/10C respectively; then, having the alkali/acid provider 14A/14B/14C of the water sample reaction equipment 10A/10B/10C provide acid or alkali to the water sample mixture in the corresponding receiving space 110A/110B/110C until the water sample mixture reaches a predetermined pH value; then, having the flocculant provider 15A/15B/15C of the water sample reaction equipment 10A/10B/10C provide flocculant to the water sample mixture in the corresponding receiving space 110A/110B/110C, so as to allow contaminants of the water sample mixture to precipitate in the receiving space 110A/110B/110C and thereby reduce turbidity; then, having the turbidity measuring device 16A/16B/16C of the water sample reaction equipment 10A/10B/10C measure turbidity of the water sample mixture in the corresponding receiving space 110A/110B/110C; then, having the coagulant concentration analysis device 30 analyze which turbidity measurement meets predetermined analysis criteria and determine its corresponding water sample reaction equipment 10A/10B/10C, wherein the concentration of coagulant of this determined water sample reaction equipment 10A/10B/10C is then used as an addition concentration of coagulant to be added to the water sample.

Therefore, the auto jartest analyzer of the present invention can replace conventional manual analysis techniques by automatically analyzing and determining an accurate concentration of coagulant to be added to a water sample to precipitate contaminants in the water sample. The automatic technique not only improves accuracy of analysis but also shortens time of analysis, making the analysis result of coagulant concentration added to the water sample immediately respond to current water quality of the water sample. This thus prevents water contamination or poor precipitation due to insufficient addition of coagulant, or avoids raise in cost due to excessive addition of coagulant.

What is claimed is:

1. An automated jar_test analyzer for analyzing a concentration of coagulant to be added to a water sample to allow contaminants in the water sample to precipitate, the automated jar_test analyzer including:
    a water sample reaction equipment group including a plurality of water sample reaction equipment, each of the water sample reaction equipment including:
    a reactor having a receiving space for receiving a predetermined amount of the water sample;
    a coagulant provider for providing coagulant of a predetermined concentration to the water sample in the receiving space so as to make the coagulant and the water sample mix and form a water sample mixture;
    a pH value measuring device for measuring a pH value of the water sample mixture in the receiving space;
    an alkali or acid provider for providing acid or alkali to the water sample mixture in the receiving space so as to make the water sample mixture have a predetermined pH value;
    a flocculant provider for providing flocculant to the receiving space, wherein the flocculant is mixed with the water sample mixture in the receiving space to make contaminants in the water sample mixture precipitate and reduce turbidity of the water sample mixture; and
    a turbidity measuring device for measuring the turbidity of the water sample mixture in the receiving space and sending out a turbidity measurement;
    coagulant providing equipment for supplying the coagulant to the coagulant provider of each of the water sample reaction equipment, wherein the coagulant providing equipment provides coagulant of different concentrations to the plurality of water sample reaction equipment respectively; and
    a coagulant concentration analysis device for receiving the turbidity measurement from the turbidity measuring device of each of the water sample reaction equipment and for analyzing all the turbidity measurements to find at least one of the turbidity measurements which meets predetermined analysis criteria, wherein the concentration of coagulant provided by the coagulant provider to the water sample reaction equipment corresponding to the found at least one turbidity measurement is added to the water sample.

2. The automated jar_test analyzer according to claim 1, wherein the water sample reaction equipment group includes first water sample reaction equipment, second water sample reaction equipment and third water sample reaction equipment, and the automated jar_test analyzer further includes a control device for controlling the first water sample reaction equipment, the second water sample reaction equipment, the third water sample reaction equipment, the coagulant providing equipment and the coagulant concentration analysis device to perform at least one set of analysis operations, wherein the control device includes:
    a setting unit for setting a standard concentration, a standard deviation, a standard turbidity range and a count value;
    a concentration calculating unit for calculating a high concentration and a low concentration according to the standard concentration and the standard deviation; and
    an execution unit for controlling the first water sample reaction equipment, the second water sample reaction equipment, the third water sample reaction equipment, the coagulant providing equipment and the coagulant concentration analysis device to perform the analysis operations including:
    having the coagulant providing equipment provide the coagulant of the low concentration to the first water sample reaction equipment, provide the coagulant of the standard concentration to the second water sample reaction equipment, and provide the coagulant of the high concentration to the third water sample reaction equipment;
    having the first water sample reaction equipment, the second water sample reaction equipment and the third water sample reaction equipment perform water sample reaction operations, such that the first water sample reaction equipment sends out a first turbidity measurement, the second water sample reaction equipment sends out a second turbidity measurement, and the third water sample reaction equipment sends out a third turbidity measurement; and
    having the coagulant concentration analysis device analyze the first turbidity measurement, the second turbidity measurement and the third turbidity measurement to see if they meet the standard turbidity range, so that the standard concentration, the high concentration and the low concentration are adjusted according to an analysis result from the coagulant concentration analysis device.

3. The automated jar_test analyzer according to claim 2, wherein the control device further includes a parameter adjusting unit, wherein when the coagulant concentration analysis device determines that all the first turbidity measurement, the second turbidity measurement and the third turbidity measurement do not meet the standard turbidity range, the parameter adjusting unit keeps the standard concentration unchanged and updates the count value to calculate a number of times of the analysis result is continuously outputted from the coagulant concentration analysis device when each of the first turbidity measurement, the second turbidity measurement and third turbidity measurement do not meet the standard turbidity range, and the concentration calculating unit updates the high concentration and the low concentration according to the standard concentration and the count value, so as to adjust parameters corresponding to the standard concentration, high concentration and low concentration, wherein the low concentration is a difference between the standard concentration and a product of the standard deviation and the count value, and the high concentration is a sum of the standard concentration and a product of the standard deviation and the count value.

4. The automated jar_test analyzer according to claim 3, wherein the at least one set of analysis operations includes a plurality of sets of analysis operations, and wherein when the number of times of the analysis result continuously outputted from the coagulant concentration analysis device that all the first turbidity measurement, the second turbidity measurement and the third turbidity measurement do not meet the standard turbidity range, reaches a predetermined number of times during each of the plurality of sets of analysis operations, the execution unit stops the analysis operations.

5. The automated jar_test analyzer according to claim 2, wherein the control device further includes a parameter adjusting unit, wherein when the coagulant concentration analysis device determines that at least two of the first turbidity measurement, the second turbidity measurement and the third turbidity measurement meet the standard turbidity range, the parameter adjusting unit selects the concentration of coagulant, which corresponds to the lowest one of the at least two of the first turbidity measurement, the second turbidity measurement and the third turbidity measurement, to be the standard concentration, and the concentration calculating unit updates the low concentration and the high concentration according to the standard concentration, so as to adjust parameters corresponding to the standard concentration, high concentration and low concentration, wherein the high concentration is a sum of the standard concentration and the standard deviation, and the low concentration is a difference between the standard concentration and the standard deviation.

6. The automated jar_test analyzer according to claim 5, wherein when the coagulant concentration analysis device determines that all the first turbidity measurement, the second turbidity measurement and the third turbidity measurement meet the standard turbidity range and are identical, the parameter adjusting unit keeps the standard concentration, the high concentration and the low concentration unchanged.

7. The automated jar_test analyzer according to claim 2, wherein the control device further includes a parameter adjusting unit, wherein when the coagulant concentration analysis device determines that only one of the first turbidity measurement, the second turbidity measurement and the third turbidity measurement meets the standard turbidity range, the parameter adjusting unit selects the concentration of coagulant, which corresponds to the determined one of the first turbidity measurement, the second turbidity measurement and the third turbidity measurement, to be the standard concentration, and the concentration calculating unit updates the low concentration and the high concentration according to the standard concentration, wherein the high concentration is a sum of the standard concentration and the standard deviation, and the low concentration is a difference between the standard concentration and the standard deviation, so as to adjust parameters corresponding to the standard concentration, high concentration and low concentration.

8. The automated jar_test analyzer according to claim 2, wherein the control device further includes a parameter adjusting unit, wherein when the coagulant concentration analysis device determines that at least two of the first turbidity measurement, the second turbidity measurement and the third turbidity measurement meet the standard turbidity range, the parameter adjusting unit selects the lowest one of the concentrations of coagulant corresponding to the at least two of the first turbidity measurement, the second turbidity measurement and the third turbidity measurement, to be the standard concentration, and the concentration calculating unit updates the low concentration and the high concentration according to the standard concentration, so as to adjust parameters corresponding to the standard concentration, high concentration and low concentration, wherein the high concentration is a sum of the standard concentration and the standard deviation, and the low concentration is a difference between the standard concentration and the standard deviation.

9. The automated jar_test analyzer according to claim 2, wherein the control device further includes a parameter adjusting unit, wherein when the coagulant concentration analysis device determines that at least two of the first turbidity measurement, the second turbidity measurement and the third turbidity measurement meet the standard turbidity range, the parameter adjusting unit selects the highest one of the concentrations of coagulant corresponding to the at least two of the first turbidity measurement, the second turbidity measurement and the third turbidity measurement, to be the standard concentration, and the concentration calculating unit updates the low concentration and the high concentration according to the standard concentration, so as to adjust parameters corresponding to the standard concentration, high concentration and low concentration, wherein the high concentration is a sum of the standard concentration and the standard deviation, and the low concentration is a difference between the standard concentration and the standard deviation.

10. The automated jar_test analyzer according to claim 2, further including a cleaning device, wherein the at least one set of analysis operations includes a plurality of sets of analysis operations, and the control device controls the cleaning device to clean the first water sample reaction equipment, the second water sample reaction equipment and the third water sample reaction equipment before or after the execution unit performs each of the plurality of sets of analysis operations.

11. The automated jar_test analyzer according to claim 10, wherein the cleaning device includes a pickling agent provider, a primary cleaning fluid provider and a secondary cleaning fluid provider, wherein the pickling agent provider provides a pickling agent to the receiving space, the primary cleaning fluid provider provides a primary cleaning fluid at a primary location to the receiving space, and the secondary cleaning fluid provider provides a secondary cleaning fluid at a secondary location to the receiving space, wherein the pickling agent, the primary cleaning fluid and the secondary cleaning fluid are for cleaning precipitate in the receiving space and the secondary cleaning fluid is further for cleaning the precipitate on the pH value measuring device.

12. The automated jar_test analyzer according to claim 11, wherein each of the water sample reaction equipment further includes a primary stirring unit and a secondary stirring unit, wherein the primary stirring unit is for providing a primary stirring force for thoroughly mixing the water sample, the coagulant, and the acid or the alkali in the receiving space, and the secondary stirring unit is for providing a secondary stirring force for mixing the water sample and the flocculant in the receiving space, wherein the secondary stirring force is weaker than the primary stirring force for better precipitation in the water sample mixture.

13. The automated jar_test analyzer according to claim 12, when the pickling agent and the primary cleaning fluid are cleaning the precipitate in the receiving space, the primary stirring unit can exert a primary stirring force on the receiving space respectively to make the pickling agent and the primary cleaning fluid being stirred in the receiving space to thereby optimize the cleaning effect on the precipitate.

14. The automated jar_test analyzer according to claim 12, the primary stirring unit and the secondary stirring unit use airflow, blades or magnets to provide the primary stirring force and the secondary stirring force respectively.

15. The automated jar_test analyzer according to claim 2, further including a cleaning device, wherein the at least one set of analysis operations includes a plurality of sets of analysis operations, and the control device controls the cleaning device to clean the first water sample reaction equipment, the second water sample reaction equipment and the third water sample reaction equipment after the execution unit performs a predetermined one of the plurality of sets of analysis operations.

16. The automated jar_test analyzer according to claim 15, wherein the cleaning device includes a pickling agent provider, a primary cleaning fluid provider and a secondary cleaning fluid provider, wherein the pickling agent provider provides a pickling agent to the receiving space, the primary cleaning fluid provider provides a primary cleaning fluid at a primary location to the receiving space, and the secondary cleaning fluid provider provides a secondary cleaning fluid at a secondary location to the receiving space, wherein the pickling agent, the primary cleaning fluid and the secondary cleaning fluid are for cleaning a precipitate in the receiving space and the secondary cleaning fluid is further for cleaning the precipitate on the pH value measuring device.

17. The automated jar_test analyzer according to claim 16, wherein each of the water sample reaction equipment further includes a primary stirring unit and a secondary stirring unit, wherein the primary stirring unit is for providing a primary stirring force for thoroughly mixing the water sample, the coagulant, and the acid or the alkali in the receiving space, and the secondary stirring unit is for providing a secondary stirring force for mixing the water sample and the flocculant in the receiving space, wherein the secondary stirring force is weaker than the primary stirring force for better precipitation in the water sample mixture.

18. The automated jar_test analyzer according to claim 17, when the pickling agent and the primary cleaning fluid are cleaning the precipitate in the receiving space, the primary stirring unit can exert a primary stirring force on the receiving space respectively to make the pickling agent and the primary cleaning fluid being stirred in the receiving space to thereby optimize the cleaning effect on the precipitate.

19. The automated jar_test analyzer according to claim 17, the primary stirring unit and the secondary stirring unit use airflow, blades or magnets to provide the primary stirring force and the secondary stirring force respectively.

20. An automatic analysis method for the automated jar_test analyzer according to claim 1, including the steps of: having the coagulant providing equipment provide the coagulant of different concentrations to the receiving space of each of the plurality of water sample reaction equipment respectively so as to form a water sample mixture of different composition in the receiving space of each of the water sample reaction equipment; having the acid or alkali provider of each of the water sample reaction equipment provide acid or alkali to the water sample mixture in the receiving space until the water sample mixture reaches a predetermined pH value; having the flocculant provider of each of the water sample reaction equipment provide the flocculant to the water sample mixture in the receiving space, so that contaminants of the water sample mixture precipitate in the receiving space and reduce turbidity; having the turbidity measuring device of each of the water sample reaction equipment measure turbidity of the water sample mixture in the receiving space; having the coagulant concentration analysis device analyze which turbidity measurement meets predetermined analysis criteria and determine its corresponding water sample reaction equipment, wherein the concentration of coagulant of the determined water sample reaction equipment is used as an addition concentration of the coagulant to be added to the water sample.

* * * * *